United States Patent [19]

Wiker et al.

[11] Patent Number: 4,731,492

[45] Date of Patent: Mar. 15, 1988

[54] PHENOL ALKYLATION PROCESS

[75] Inventors: Steven L. Wiker, Orangeburg; S. Wendell Holmes, Jr., Columbia, both of S.C.; Dixie E. Goins, Baton Rouge, La.

[73] Assignee: Ethyl Corporation, Richmond, Va.

[21] Appl. No.: 21,754

[22] Filed: Mar. 4, 1987

[51] Int. Cl.$^4$ ............................................. C07C 37/14
[52] U.S. Cl. .................................... 568/794; 568/780; 568/790
[58] Field of Search ............... 568/780, 781, 784, 785, 568/789, 790, 794

[56] References Cited

U.S. PATENT DOCUMENTS

| 3,200,157 | 8/1965 | Buls et al. ........................... | 568/789 |
| 3,290,389 | 12/1966 | Hahn ................................... | 568/794 |
| 3,367,981 | 2/1968 | Napolitano .......................... | 568/789 |
| 3,670,030 | 6/1972 | Sparks ................................. | 568/794 |
| 3,831,898 | 4/1958 | Ecke .................................... | 568/794 |
| 4,260,833 | 4/1981 | Firth .................................... | 568/794 |
| 4,599,465 | 7/1986 | Tamaru ................................ | 568/781 |

FOREIGN PATENT DOCUMENTS

| 700451 | 12/1968 | Canada ................................ | 568/789 |
| 1815846 | 1/1970 | Fed. Rep. of Germany ...... | 568/781 |
| 2215170 | 1/1973 | Fed. Rep. of Germany ...... | 568/781 |
| 0178835 | 9/1985 | Japan .................................. | 568/794 |

Primary Examiner—Werren B. Lone
Attorney, Agent, or Firm—Donald L. Johnson; John F. Sieberth; Joseph D. Odenweller

[57] ABSTRACT

A process of ortho-alkylating arylhydroxides, e.g., phenol, by passing a mixture of arylhydroxide, olefin and an inert hydrocarbon diluent in the liquid phase through a bed of activated alumina at an elevated temperature and pressure. Conversion and selectivity is improved over that obtained without the diluent.

20 Claims, No Drawings

PHENOL ALKYLATION PROCESS

BACKGROUND OF THE INVENTION

Phenols are readily alkylated by reaction of phenol with olefin in contact with an acidic catalyst. This produces a mixture of mono, di and tri-alkylphenols and all positional isomers, mainly 2-alkyl, 4-alkyl, 2,4-dialkyl and 2,4,6-trialkyl. Ecke et al. U.S. Pat. No. 2,831,898 describe a method of selectively orthoalkylating phenol by reaction with an olefin using an aluminum phenoxide catalyst. The product is mainly 2,6-dialkylphenol containing minor amounts of 2-alkylphenol.

Hahn U.S. Pat. No. 3,290,389 describes a process for alkylating phenol with olefins under pressure using a gamma alumina catalyst at 200–400° C. With propylene and butene, the products were mainly 2-alkyl and 2,6-dialkylphenol.

Napolitano U.S. Pat. No. 3,367,981 is similar to Hahn but expands the useful catalyst to include all transitional aluminas.

Sparks U.S. Pat. No. 3,670,030 describes an improvement in the gamma alumina catalyzed ortho-alkylation of phenol with olefins in which catalyst life is prolonged by adding a controlled amount of water to the phenol. A preferred water content is 1000–3000 ppm.

Tamura et al. U.S. Pat. No. 4,599,465 teach that catalytic activity of gamma alumina can be increased by reducing the water content of the phenol below 250 ppm. This requires the additional step of removing water from commercially available phenol by methods such as distillation, blowing inert gas through the heated phenol, absorbing water with a desiccant such as a molecular sieve, zeolite, alumina or ion exchange resin. The test data reports time required to reach a 70% conversion of in a batch operation which was less with dried phenol than with wet phenol.

A need exists for a process of ortho-alkylating phenol with olefin using an activated alumina catalyst that will give both the high catalytic activity and selectivity sought by Tamura et al. and a prolonged catalyst life sought by Sparks.

SUMMARY OF THE INVENTION

It has now been discovered that arylhydroxides having an unsubstituted ortho position can be continuously ortho-alkylated by reaction with an olefin in contact with an alumina catalyst at a high conversion (approx. 60% with isobutylene) and high selectivity to mono-ortho-alkylarylhydroxide (approx. 90% with phenol) with a very long catalyst life (at least 630 hours) by mixing or co-feeding an inert hydrocarbon diluent with the arylhydroxide and continuously feeding the arylhydroxide and diluent together with an olefin in the liquid phase through an activated alumina catalyst bed at an elevated temperature and pressure sufficient to maintain the liquid phase.

Conversion is the mole percent of the arylhydroxide that is reacted to form any product. Unconverted arylhydroxide can be recovered by distillation and recycled. Selectivity is the mole ratio of the desired product to the undesired products in the converted phenol.

DESCRIPTION OF THE PREFERRED EMBODIMENTS

A preferred embodiment of the invention is a process for mono-orthoalkylating phenol, said process comprising continuously passing a mixture of said phenol, and olefin and an inert hydrocarbon diluent in the liquid phase through an activated alumina bed at an elevated temperature and under sufficient pressure to maintain said phenol, hydrocarbon diluent and olefin in the liquid phase.

The process is conducted by mixing arylhydroxide and an inert diluent and continuously feeding the mixture together with an olefin in the liquid phase to a pressure reactor containing a bed of activated alumina catalyst. Alternatively the arylhydroxide and inert diluent can be separately co-fed to the pressure reactor. The pressure reactor is preferably an extended cylindrical or tubular reactor wherein the reactants and diluents are pumped in at one end and withdrawn at the opposite end.

Any arylhydroxide having an unsubstituted ortho position capable of being alkylated can be used. Representative examples include ortho-cresol, meta-cresol, para-cresol, p-chlorophenol, o-chlorophenol, p-bromophenol, 4-methoxyphenol, o-ethylphenol, p-ethylphenol and the like. The most preferred arylhydroxide is the compound phenol.

An important advantage of the present process is that it operates well on standard commercial grade phenol. In the process described by Sparks U.S. Pat. No. 3,670,030 it was necessary to add water to the phenol to a level of 500–5000 preferably 1000–3000 ppm, to obtain a useful catalyst life. In Tamura et al. U.S. Pat. No. 4,599,465 it was necessary to dry the phenol to a water level not over 250 ppm, more preferably not over 150 ppm in order to obtain the desired catalyst selectivity and activity. It has been found and will be shown that the present process is both selective and provides a long catalyst life using commercial grade phenol without drying or adding water although this can be done if one so desires.

Any inert aliphatic or aromatic hydrocarbon that is liquid at reaction conditions can be used. Some examples are pentane, hexane, cyclohexane, heptane, octane, cyclooctane, nonane, decane, benzene, toluene, xylene, mesitylene, ethyl benzene, diethylbenzene and the like including mixtures thereof.

The preferred inert hydrocarbon diluents are the aromatic hydrocarbons such as benzene, toluene, o-xylene, m-xylene, p-xylene, durene, mesitylene, ethylbenzene, 1,3-diethylbenzene, 1,4-diethylbenzene, isobutylbenzene, tert-butylbenzene, sec-butylbenzene, isopropylbenzene and the like including mixtures thereof. Preferably the aromatic hydrocarbon diluent boils in the range of 80°–200° C. at atmospheric pressure. The most preferred inert diluent is xylene, especially mixtures of xylene isomers.

Aliphatic hydrocarbons can also be used as the diluent. Preferred aliphatic hydrocarbons boil at 60°–200° C. at atmospheric pressure.

The phenol-diluent composition can vary over a wide range. A useful range is about 10–90 weight percent phenol, and the balance inert diluent. A more preferred feed mixture is 30–70 weight percent phenol and the most preferred feed is about 50 weight percent phenol and the balance inert diluent.

Equivalent results can be achieved by separately feeding phenol and diluent at a weight ratio of 1:9 to 9:1, more preferably 3:7 to 7:3 and most preferably 1:1.

The process can be conducted with any of the activated aluminas known to catalyze the alkylation of phenols by reaction with olefin. These include all those reported by Hahn U.S. Pat. No. 3,290,389; Napolitano U.S. Pat. No. 3,367,981; Sparks U.S. Pat. No. 3,670,030 and Tamura et al. U.S. Pat. No. 4,599,465 which are incorporated herein by reference. The most preferred catalyst are activated gamma alumina which may contain other ingredients such as alkali metal, alkaline earth metal, halogen and the like as mentioned by Sparks. Aluminas can be activated by heating them in the range of about 400–1000° C., more preferably in the range of 500°–700° C. for a period from about 15 minutes up to 8 hours or more. Suitable gamma alumina catalysts are available commercially.

Any olefin that will react with phenol to introduce a substituent group can be used. Preferably the olefin is a mono-olefinic hydrocarbon containing 2-12 carbon atoms such as ethylene, propylene, isobutylene, n-butene, n-pentene, iso-pentene, 3-methyl-1-butene, 1-hexene, 2-hexene, 3-hexene, 2-methyl-1-pentene, 3-methyl-1-pentene, 2-ethyl-1-hexene, 1-octene, 2-octene, 1-dodecene, 2-ethyl-1-decene, styrene, alpha-methyl styrene, cyclopentene, cyclohexene, cyclooctene and the like including mixtures thereof.

The preferred olefin reactants are aliphatic mono-olefinic hydrocarbons containing 3-12 carbon atoms such as propylene, 1-butene, 2-butene, isobutylene, 1-pentene, 2-pentene, 3-methyl-1-butene, 1-hexene, 2-hexene and the like including mixtures thereof. The process is especially useful with tert-olefins containing 4-12 carbon atoms such as isobutylene, isopentene, 2-methyl-1-butene, 2-ethyl-1-butene, 2-methyl-1-pentene, 2-ethyl-1-pentene, 3-methyl-2-pentene, 2-ethyl-1-octene, 2-methyl-1-decene, 3-ethyl-2-decene and the like.

The most preferred olefin reactant is isobutylene.

The ratio of olefin to phenol fed to the reactor can vary over a wide range. A useful range is about 0.8–10 moles of olefin per mole of phenol. A more preferred range is about 0.9–2 moles of olefin per mole of phenol. A still more preferred range is about 1–1.5 moles of olefin per mole of phenol. The most preferred ratio is about 1:1.

The continuous reactor is maintained at a temperature high enough to cause the reaction to proceed at a reasonable rate but not so high as to cause decomposition or to substantially increase the amount of undesirable by-products. A useful operating temperature is about 100°–250° C. A more preferred operating temperature is about 120°–200° C. A still more preferred operating temperature is about 130°–185° C. and most preferably 140°–185° C.

In practice, the process is generally conducted by starting the process with a freshly activated alumina at the lower end of the preferred temperature range, e.g. 130°–140° C. As the conversion starts to drop, the temperature is gradually or incrementally increased to compensate. As the operating temperature is increased to maintain conversion, the amount of by-product will increase thus lowering selectivity. The maximum temperature is a matter of economics. When selectivity drops below 10:1 it is generally not economical to continue operation even if conversion remains high because too much by-product is formed. With isobutylene the process is usually started at about 140° C. to achieve a 60% conversion and over 15:1 selectivity to 2-tert-butylphenol. The temperature is very slowly increased to about 185° C. to maintain conversion at about 60%. This has been shown to require at least 600 hours. The selectivity to 2-tert-butylphenol is closely monitored and when this drops below about 10-11:1, the process is stopped and the catalyst regenerated by heating to 400°–1000° C. in a current of air. Such activation processes are well known.

The pressure within the reactor is not an independent variable but depends upon the temperature and vapor pressure of the feed stock at that temperature. The pressure should be sufficient to maintain the reaction mixture in the liquid phase or at least mainly in the liquid phase. A useful pressure range in which to investigate is about 50–2000 psig. In the most preferred embodiment using phenol, xylene and isobutylene, the pressure is in the range of about 300–1000 psig.

The reactor is preferably an elongated, cylindrical or tubular reactor filled with catalyst. The feed is introduced at one end and passes through the catalyst bed in a plug-flow manner and is discharged at the opposite end.

The volume of the catalyst bed should be sufficient to provide an adequate contact time with the reactor at the desired production rate. Contact times in the range of about 5–30 minutes generally gives acceptably high conversions. A preferred average contact time is about 5–20 minutes.

The following examples serve to show how the process is conducted and to compare it to a similar process conducted without inert diluent.

EXAMPLE 1

Comparative Example

This example shows the prior art method of conducting a phenol alkylation without use of an inert diluent.

Two tubular sections 0.742 inch inside diameter by 108 inches long were connected in series to form the reactor. Each section was charged with approximately 400 grams of activated gamma alumina (UOP SB-2W). Activation was by heating the alumina in air at 400°–500° C. for 4 hours. Phenol was pumped into one end of the reactor at a rate of 74 grams per minute while the reactor was held initially at about 140° C. and periodically increased in temperature to maintain conversion. Isobutylene was pumped in at a rate which maintained an isobutylene:phenol mole ratio of about 1:1. Pressure in the reactor was held constant at about 400 psig by means of the discharge valve. Average contact time with the catalyst bed was 7.0 minutes. The composition of the discharged reaction mixture was analyzed by gas chromatography. The progress of the reaction is shown in the following table based on the analysis of the product.

TABLE 1

|  | Start | HOURS | | | | | |
|---|---|---|---|---|---|---|---|
|  |  | 45 | 60 | 85 | 105 | 150 | 170 |
| Temp. (°C.) | 140° | 140 | 145 | 150 | 160 | 170 | 180° |
| Conversion[1] (%) | 46.5 | 37 | 43.5 | 38 | 44.5 | 34 | 36 |
| Selectivity[2] | 10.4 | 10.0 | 9.5 | 14.9 | 11.0 | 9.5 | 8.3 |

[1] Mole percent of phenol feed that is reacted to form a different compound

[2] $\dfrac{\text{moles 2-tert-butylphenol}}{\text{moles 2,4-di-tert-butylphenol + 4-tert-butylphenol}}$

EXAMPLE 2

This example shows the process of the present invention. The catalyst was the same gamma alumina used in Example 1. The feed to the reactor was (1) a 50 weight percent solution of phenol in xylene and (2) isobutylene which was at a rate to provide an isobutylene:phenol mole ratio of 1:1. The reactor was held at 400 psig. The average contact time was 13.0 minutes. The initial temperature was 140° C. which was periodically increased to maintain conversion. The results are shown in the following Table 2.

TABLE 2

| | Start | 50 | 150 | 200 | 300 | 400 | 500 | 550 | 600 | 630 |
|---|---|---|---|---|---|---|---|---|---|---|
| | | | | | HOURS | | | | | |
| Temp. (°C.) | 140° | 155 | 155 | 165 | 165 | 170 | 175 | 180 | 185 | |
| Conversion (%) | 50 | 72.5 | 41 | 70 | 64 | 57.5 | 44 | 56 | 75 | 76.5 |
| Selectivity | 33.3 | 18.2 | 21.1 | 13.9 | 15.4 | 18.2 | 16.9 | 16.9 | 11.1 | 11.1 |

The comparative tests show that without the use of an inert diluent (Example 1) conversion never exceeded 50% and at 170 hours had dropped to 36%. Selectivity started at 10.4 and except for one brief excursion to 14.9 stayed close to 10 dropping to 8.3 at 170 hours. At 170 hours the conversion was only 36% and selectivity was 8.3 so the run was terminated.

Following the present process (Example 2) the initial conversion was 50% which increased to 72.5% at 155° C. Conversion stayed above 50% through most of the run and was still 76.5% after 630 hours (over 26 days). Initial selectivity to o-tert-butylphenol was at a high 33.3 and stayed above 15 through most of the run before dropping to 11.1 at the end. These results show that the present process has achieved its goal of obtaining a long catalyst life at high conversion while at the same time retaining high selectivity.

We claim:

1. A process for mono-orthoalkylating an arylhydroxide having an unsubstituted ring position ortho with respect to the hydroxy group, said process comprising continuously passing a mixture of said arylhydroxide and olefin in a mole ratio of 0.8–10 moles of olefin per mole of arylhydroxide and an inert hydrocarbon diluent in an amount such that the arylhydroxide:diluent ratio is about 10–90 weight percent arylhydroxide and 90–10 weight percent diluent in the liquid phase through an activated alumina bed at an elevated temperature of 120°–200° C. and under a pressure in the range of 50–2000 psig which is also sufficient to maintain said arylhydroxide, hydrocarbon diluent and olefin in the liquid phase.

2. A process of claim 1 wherein said arylhydroxide is phenol.

3. A process of claim 2 conducted at a temperature of about 130°–200° C.

4. A process of claim 3 wherein the average contact time of said mixture with said activated alumina bed is in the range of 5–30 minutes.

5. A process of claim 2 wherein said olefin is a mono-olefinic hydrocarbon containing 2–12 carbon atoms.

6. A process of claim 5 conducted at a temperature of about 130°–200° C.

7. A process of claim 6 wherein said mono-olefinic hydrocarbon, is isopropylene.

8. A process of claim 6 wherein said mono-olefinic hydrocarbon is n-butene.

9. A process of claim 6 wherein said mono-olefinic hydrocarbon is a tert-olefin containing 4–12 carbon atoms.

10. A process of claim 9 wherein said tert-olefin is isobutylene.

11. A process of claim 2 wherein said activated alumina is an activated gamma alumina.

12. A process of claim 11 wherein said inert hydrocarbon is an aromatic hydrocarbon boiling in the range of about 80°–200° C.

13. A process of claim 11 wherein said inert hydrocarbon is an aliphatic hydrocarbon boiling in the range of about 60°–200° C.

14. A process of claim 12, wherein said olefin is a mono-olefinic hydrocarbon containing 2–12 carbon atoms.

15. A process of claim 14 wherein said aromatic hydrocarbon is xylene.

16. A process of claim 15 wherein said olefin is propylene.

17. A process of claim 15 wherein said olefin is n-butene.

18. A process of claim 15 wherein said olefin is isobutylene.

19. A process of claim 18 conducted at a temperature of about 140°–185° C.

20. A process of claim 19 wherein the average contact time of said isobutylene and phenol with said gamma alumina is in the range of about 5–30 minutes.

* * * * *

UNITED STATES PATENT AND TRADEMARK OFFICE
CERTIFICATE OF CORRECTION

PATENT NO. : 4,731,492
DATED : MARCH 15, 1988
INVENTOR(S) : STEVEN L. WIKER ET AL.

It is certified that error appears in the above-identified patent and that said Letters Patent is hereby corrected as shown below:

Column 1, line 36 reads "conversion of in" and should read -- conversion of phenol in --.

Column 1, line 48 reads "an alumina" and should read -- an activated alumina -- .

Column 5, line 35 reads "a moxture of" and should read -- a mixture of -- .

Column 6, line 17 reads "hydrocarbon, is" and should read -- hydrocarbon is -- .

Signed and Sealed this

Twenty-sixth Day of July, 1988

Attest:

DONALD J. QUIGG

Attesting Officer

Commissioner of Patents and Trademarks